US00PP14744P3

(12) United States Plant Patent
Yamaguchi

(10) Patent No.: US PP14,744 P3
(45) Date of Patent: May 4, 2004

(54) *AUCUBA JAPONICA* PLANT NAMED 'NATSU-NO-KUMO'

(50) Latin Name: *Aucuba japonica*
Varietal Denomination: Natsu-No-Kumo

(75) Inventor: Seiju Yamaguchi, Mizunami (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/107,906

(22) Filed: Mar. 26, 2002

(65) Prior Publication Data

US 2003/0188357 P1 Oct. 2, 2003

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Annette H Para
(74) *Attorney, Agent, or Firm*—Christie, Parker & Hale, LLP

(57) ABSTRACT

A new plant variety of *Aucuba japonica* characterized by its white new growth in spring, gradually changing to cream and eventually green late in the growing season.

1 Drawing Sheet

Figure 1:
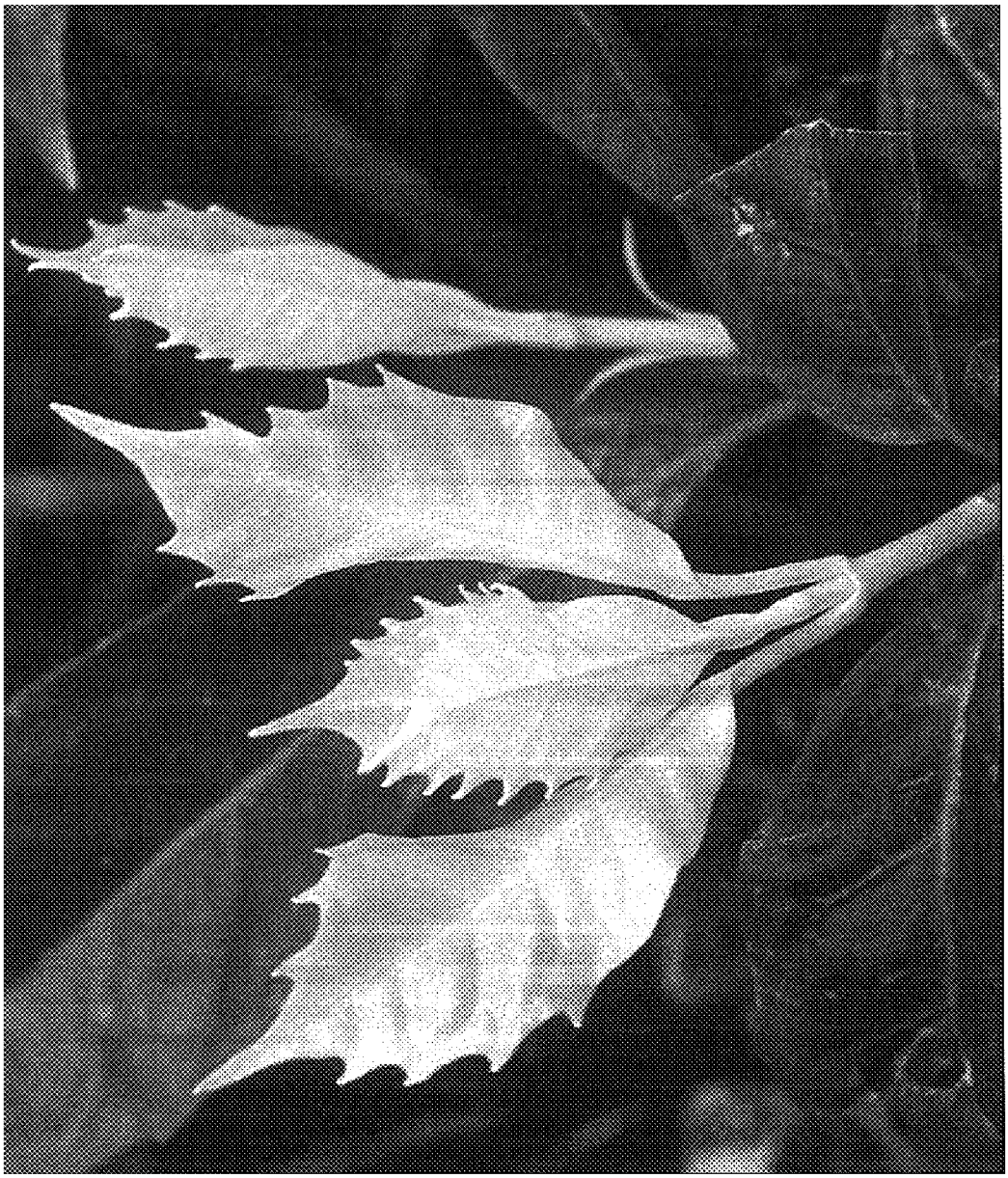

Classification: The present invention relates to a new *Aucuba japonica* Thunb.

Variety denomination: The varietal denomination of the new variety is 'Natsu-No-Kumo'.

BACKGROUND OF THE INVENTION

The present invention relates to a new and distinct variety of *Aucuba japonica* Thunb. plant, which was discovered as a naturally occurring, whole-plant variant in a cultivated planting of unnamed, unpatented *Aucuba japonica* in Mizunami City, Gifu Prefecture, Japan.

The genus Aucuba is included in the family Cornaceae (alternately Aucubaceae), which comprises about 10 genera and 90 species of widely distributed trees and shrubs, native mostly to the temperate regions of North America and Asia. Aucuba comprises 3 to 7 species of dioecious, evergreen shrubs, native to temperate areas from the Himalayas to Japan, many of which possess desirable ornamental characteristics.

*Aucuba japonica* is an evergreen shrub with many ornamental attributes. It generally has green foliage or cultivars with varying degrees of spotted or mottled variegation.

SUMMARY OF THE INVENTION

The new variety was discovered as a seedling in a cultivated planting of *Aucuba japonica* and differs from its parent by its white new growth in spring, gradually changing to cream and eventually green by late in the growing season. Asexual reproduction of the new variety by cuttings, performed in Mizunami City, Japan, York Haven, Pa. and Vacaville, Calif., have confirmed that the distinctive characteristics of the new variety are stable and transmitted to succeeding generations, and the new variety reproduces true to type.

COMPARISON WITH PARENTS

'Natsu-No-Kumo' is distinguished from its parents and all other varieties of *Aucuba japonica* of which I am aware by its white new growth in spring, gradually changing to cream and eventually green late in the growing season.

BRIEF DESCRIPTION OF ILLUSTRATION

The accompanying illustration shows a specimen of the new cultivar in a photo illustration as true to color as is reasonably possible to make in an illustration of this character.

FIG. 1 illustrates the distinctive new white foliage of 'Natsu-No-Kumo'.

DETAILED DESCRIPTION OF THE NEW VARIETY

'Natsu-No-Kumo' has not been observed under all possible environmental, cultural and light conditions. The following observations and descriptions are of plants grown in Lewisberry, Pa. In this description, color references are to The Royal Horticultural Society Colour Chart (1995) and terminology used in the color descriptions herein refers to plate numbers in this color chart. Phenotypic expression may vary with light intensity, cultural and environmental conditions.

Classification:

*Botanical.*—*Aucuba japonica. Thunb.* 'Natsu-No-Kumo'.

*Parentage.*—Whole-plant variant in a cultivated planting of unnamed, unpatented *Aucuba japonica.*

*Propagation.*—Cuttings.

Plant:

*Size.*—About 2 m. tall.

*Habit.*—Upright shrub.

*Branching.*—Freely branching. Typical # Branches: About 15 to 20 on mature specimen. Size: To about 1 m. Diameter: Approximately 1 cm. Color: Near Yellow-Green Group 147B. Color of New shoots: Near Yellow-Green Group 157B.

Leaf:

*Shape.*—Elliptic to narrow — ovate.

*Apex.*—Acuminate to cuspidate.

*Base.*—Cuneate.

*Leaf size.*—About 18 cm long and 6 cm wide.

*Arrangement.*—Opposite.

*Margin.*—Serrated.

*Texture/substance.*—Coriaceous, glossy.

*Color.*—The following color readings are of 4 year-old specimens in 5 gallon nursery containers grown in Lewisberry, Pa. Young Foliage Upper side: Near White Group 155A. Underside: Near White Group 155A. Mature Foliage Upper side: Near 147A. Underside: Near Group 147B.

*Venation.*—Pattern: Alternately pinnate. Coloration New Foliage Upper surface: Near 155A. Under surface: Near 155A. Mature Foliage Upper surface: Near 147D. Under surface: Near 144B.

*Petioles.*—Size: About 8 mm. Color: Near 147B. Internodes: About 5 cm.

*Hardiness.*—USDA Zone 7 (0° F. to 10° F.).

*Vigor.*—Fast growing.

*Pests/diseases.*—None noted.

*Infloresence.*—None yet observed

*Reproductive organs.*—None yet observed.

I claim:

1. A new and distinct variety of *Aucuba japonica* of the variety substantially as shown and described.

* * * * *